US010287550B2

(12) United States Patent
An et al.

(10) Patent No.: US 10,287,550 B2
(45) Date of Patent: May 14, 2019

(54) SERUM-FREE CHEMICALLY DEFINED CELL CULTURE MEDIUM

(71) Applicant: StemRD, Inc., Burlingame, CA (US)

(72) Inventors: Songzhu An, Foster City, CA (US); Yanan Zhu, Navato, CA (US)

(73) Assignee: StemRD, Inc., Burlingame, CA (US)

( * ) Notice: Subject to any disclaimer, the term of this patent is extended or adjusted under 35 U.S.C. 154(b) by 212 days.

(21) Appl. No.: 15/166,965

(22) Filed: May 27, 2016

(65) Prior Publication Data

US 2016/0281060 A1 Sep. 29, 2016

Related U.S. Application Data

(63) Continuation of application No. 13/703,296, filed as application No. PCT/US2011/001088 on Jun. 16, 2011, now abandoned.

(60) Provisional application No. 61/397,847, filed on Jun. 17, 2010.

(51) Int. Cl.
| | |
|---|---|
| *C12N 5/00* | (2006.01) |
| *A61K 35/28* | (2015.01) |
| *A61K 35/32* | (2015.01) |
| *C12N 5/077* | (2010.01) |
| *C12N 5/0775* | (2010.01) |

(52) U.S. Cl.
CPC ............ *C12N 5/0662* (2013.01); *A61K 35/28* (2013.01); *A61K 35/32* (2013.01); *C12N 5/0037* (2013.01); *C12N 5/0655* (2013.01); *C12N 5/0663* (2013.01); *C12N 5/0665* (2013.01); *C12N 5/0667* (2013.01); *C12N 2500/24* (2013.01); *C12N 2500/25* (2013.01); *C12N 2500/36* (2013.01); *C12N 2500/38* (2013.01); *C12N 2500/90* (2013.01); *C12N 2501/105* (2013.01); *C12N 2501/11* (2013.01); *C12N 2501/115* (2013.01); *C12N 2501/135* (2013.01); *C12N 2501/15* (2013.01); *C12N 2501/33* (2013.01); *C12N 2501/39* (2013.01); *C12N 2501/415* (2013.01); *C12N 2501/825* (2013.01); *C12N 2506/1346* (2013.01)

(58) Field of Classification Search
None
See application file for complete search history.

(56) References Cited

U.S. PATENT DOCUMENTS

| 5,908,782 A | 6/1999 | Marshak et al. |
| 7,723,106 B2 | 5/2010 | Hwang et al. |
| 7,955,846 B2 | 6/2011 | Tilly et al. |
| 2002/0169122 A1 | 11/2002 | Majumdar et al. |
| 2005/0266553 A1 | 12/2005 | Pebay |
| 2006/0194321 A1 | 8/2006 | Colman et al. |
| 2007/0287176 A1 | 12/2007 | Rezania |
| 2009/0233354 A1 | 9/2009 | Furcht et al. |
| 2010/0047351 A1 | 2/2010 | Zeitlin et al. |
| 2010/0068806 A1 | 3/2010 | Laine et al. |
| 2010/0093053 A1 | 4/2010 | Oh et al. |

FOREIGN PATENT DOCUMENTS

| EP | 1988159 | 11/2008 |
| WO | WO 2008/133904 | 11/2008 |

OTHER PUBLICATIONS

Lu, Wenyan, et al. "R-spondin1 synergizes with Wnt3A in inducing osteoblast differentiation and osteoprotegerin expression." FEBS letters 582.5 (2008): 643-650 (Year: 2008).*
U.S. Appl. No. 61/397,847, filed Jun. 17, 2010.
International Patent Cooperation Treaty Patent Application No. PCT/US2011/001088, filed Jun. 16, 2011.
Chimal-Monroy, et al. Differential effects of transforming growth factors β 1, β 2, β 3 and β 5 on chondrogenesis in mouse limb bud mesenchymal cells. Int. J. Dev. Biol., 1997, 41:91-102.
Chimal-Monroy, et al. Differential effects of transforming growth factors beta 1, beta 2, beta 3 and beta 5 on chondrogenesis in mouse limb bud mesenchymal cells. Int. J. Dev. Biol., 1997, 41:91-102; Abstract.
U.S. Appl. No. 13/703,296, filed Dec. 10, 2012.
Baldessarini et al. Decreased risk of suicides and attempts during long-term lithium treatment: a meta-analyticreview. Bipolar Disorders, Oct. 2006, 8:625-639.
Cohen et al. Gsk3 Inhibitors: Development and Therapeutic Potential. Nature Reviews, Jun. 2004, vol. 3, pp. 479-487.
Crabtree et al. NFAT Signaling: Choreographing the Social Lives of Cells. Cell, Apr. 2002, vol. 109, pp. S67-S79.
De Boer et al. Effects on Wnt signaling on proliferation and differentiation of human mesenchymal stem cells. Tissue Engineering, 2004, 10(3-4):393-401.
Einat et al. Augmentation of lithium's behavioral effects by inositol uptake inhibitors. J Neural Transm, Mar. 1998, vol. 105, Issue 1, pp. 31-38 (abstract only).
Ghasemi et al. A role for nitrergic system in the antidepressant-like effects of chronic lithium treatment in the mouse forced swimming test. Behavioural Brain Research 200 (2009) 76-82.
Goetzl, et al. Lysophospholipid growth factors and their G protein-coupled receptors in immunity, coronary artery disease, and cancer. The Scientific World Journal, Feb. 2002, 2:324-38.
Hanlon et al. Lithium Chloride as a Substitute for Sodium Chloride in the Diet; observations on its toxicity.J of the American Medical Association, Mar. 1949, 139(11):688-692.
Jin et al. Wnt and beyond Wnt: Multiple mechanisms control the transcriptional property of β-catenin. Cellular Signalling, vol. 20, Issue 10, Oct. 2008, pp. 1697-1704.

(Continued)

*Primary Examiner* — Robert J Yamasaki
(74) *Attorney, Agent, or Firm* — Craig R. Miles; CR Miles P.C.

(57) ABSTRACT

Embodiments of chemically defined cell culture media containing nutrients and growth factors free of any serum for culturing cells such as mesenchymal stem cells and methods of using embodiments of the cell culture medium for expanding cell populations such as mesenchymal stem cells while maintaining a pluripotent phenotype and methods of inducing chondrogenesis and osteogenesis of mesenchymal stem cells by admixing differentiation factors into embodiments of the cell culture medium.

23 Claims, 9 Drawing Sheets

(56) References Cited

OTHER PUBLICATIONS

Kim et al. R-Spondin family members regulate the Wnt pathway by common mechanism. Moleculalr biology of the Cell, 2008, 19(6):2588-2596.

Klein et al. A molecular mechanism for the effect of lithium on development. Proc. Natl. Acad. Sci., Aug. 1996, vol. 93, pp. 8455-8459.

Massot et al. 5-HT1B Receptors: A Novel Target for Lithium. Possible Involvement in Mood Disorders. Neuropsychopharmacology, 1999, vol. 21, No. 4, pp. 530-541.

Satija et al. High Throughput Transcriptome Profiling of Lithium Stimulated Human Mesenchvmal Stem Cells Reveals Priming towards Osteoblastic Lineage. PLoS One, Jan. 30, 2013, vol. 8, Issue 1, pp. 1-12.

Scheuch et al. Lithium modulated tryptophan hydroxylase 2 gene expression and serotonin release in primary cultures of serotonergic raphe neurons. Brain Research, Jan. 2010, 1307:14-21.

Shinmura et al. RSPO fusion transcripts in colorectal cancer in Japanese population. Mol Biol Rep, DOI 10.1007/s11033-014-3409-x, published online May 2014, total 10 pages.

The Wnt Homepage At Stanford. How to activate and detect Wnt signaling; website, www.stanford.edu/group/nusselab/cgi-bin/wnt/reports, originally downloaded Jul. 23, 2014, 2 total pages.

Toledano et al. 3_-5_ Phosphoadenosine phosphate is an inhibitor of PARP-1 and a potential mediator of the lithium-dependent inhibition of PARP-1 in vivo.
Biochem. J., Apr. 2012, 443, pp. 485-490.

Verbov et al. A Case of Lithium Intoxication. Postgrad. Med. J., Apr. 1965, No. 41, Issue 474, pp. 190-192.

Yenush et al. A novel target of lithium therapy. FEBS Letters, 2000, 467:321-325.

Yin et al. Nuclear receptor Rev-ebalpha is critical lithium-sensitive component of the circadian clock, Science, Feb. 2006, 311 (5763): 1002-5.

Yin et al. Nuclear receptor Rev-erba: a heme receptor that coordinates circadian rhythm and metabolism. Nuclear Receptor Signaling, 2010, vol. 8, pp. 1-6.

York et al. Definition of a metal-dependent/Li+-inhibited phosphomonoesterase protein family based upon a conserved three-dimensional core structure. Proc. Natl. Acad. Sci. USA, Biochemistry, 1995, 92, pp. 5149-5153.

\* cited by examiner

SERUM-FREE CHEMICALLY DEFINED CELL CULTURE MEDIUM

This United States Patent Application is a continuation of U.S. patent application Ser. No. 13/703,296, filed Dec. 10, 2012, which is the United States National Stage of International Patent Cooperation Treaty Patent Application No. PCT/US2011/001088, filed Jun. 16, 2011, which claims the benefit of U.S. Provisional Patent Application No. 61/397,847 filed Jun. 17, 2010, each hereby incorporated by reference herein.

I. TECHNICAL FIELD

Generally, a serum-free chemically defined cell culture medium for the culture of cells. Specifically, a serum-free chemically defined cell culture medium for the culture of mesenchymal stem cells which allows expansion while maintaining a pluripotent phenotype from which chondrocytes and osteocytes can be derived and methods of using such populations of expanded mesenchymal stem cell populations for the treatment of disorders benefitted by administration of a therapeutic amount of such expanded and differentiated mesenchymal stem cell populations.

II. BACKGROUND

Bone and cartilage transplantations are performed in reconstruction of bone and cartilage segments in plastic surgery, traumatic surgery or after the removal of neoplastic lesions. Currently, human tissues from an autologous source, or from living or deceased donors have been used for this purpose. With the advance of stem cell research, bone and cartilage cells derived from mesenchymal stem cells are becoming cellular sources for skeletal repair.

Mesenchymal stem cells (MSCs) can be found in certain tissues of the body, such as the bone marrow, blood, dermis and periosteum. They possess the ability to differentiate to other types of cells, and therefore may contribute to the healing of the tissues after injuries. MSCs can be isolated and purified from the bone marrow and culturally expanded in-vitro.

Presently, the in-vitro expansion of MSCs takes place in culture medium supplemented with fetal bovine serum (hereinafter "FBS") or with human autologous serum, or substantially similar or equivalent serum (also referred to as "serum"). However, the presence of animal or human serum in MSC cultures has certain disadvantages and limitations in view of the potential therapeutic applications of these cultures. Firstly, bovine serum, human serum, or other animal serum may contain blood born pathogens, such as viruses and mad cow prions, bovine spongiform encephalopathy ("BSE"), or the like. Secondly, bovine serum invokes antibody generation to xenobiotic proteins which may invoke immune responses in recipient patients. Thirdly, bovine serum exhibits lot to lot variations which can result in inconsistent performance.

Clearly, cell culture media containing only chemically defined substances and free of serum and xenobiotics may be highly desired for the culture of MSCs (and other cells) assuming that the inventive cell culture media and methods of utilizing the inventive cell culture media afford both expansion of cells including MSCs and further affords differentiation of MSCs in culture.

III. DISCLOSURE OF INVENTION

Accordingly, a broad object of the invention can be to provide one or more embodiments of an inventive chemically defined serum-free medium (also referred to as the "serum-free medium") for cell culture and as to particular non-limiting embodiments of the inventive serum-free media for expanding populations of MSCs in vitro including but not limited to human MSCs ("hMSCs").

Another broad object of the invention can be to provide embodiments of a serum-free medium which contains a combination of chemical components capable of supporting MSC viability, proliferation and differentiation in ex-vivo in-vitro cell culture and in particular MSC in-vitro culture without containing any serum, such as fetal bovine serum, autologous serum, or other animal serum. Additionally, embodiments of the inventive media can be utilized to support MSC viability, proliferation and differentiation with substantially similar or greater effectiveness or results as compared to conventional cell culture media containing serum.

Another broad object of the invention can be methods of culturing cells such as MSCs and in particular human MSCs in the inventive media resulting in expansion of MSC populations and differentiation of MSCs to produce chondrocytes or osteocytes.

Another broad object of the invention can be a method of culturing cells such as MSCs on a negatively charged plastic surface such as the negatively charged surface of polystyrene plastic which avoids the step of coating the surface with fibronectin, or the like.

Naturally, further objects of the invention are disclosed throughout other areas of the specification, drawings, photographs, and claims.

IV. BRIEF DESCRIPTION OF THE DRAWINGS

FIG. 1 provides images which compare cell culture morphology between hMSCs cultured in conventional medium containing 10% FBS and hMSCs cultured in a particular embodiment of the inventive serum-free medium.

Figure 4:
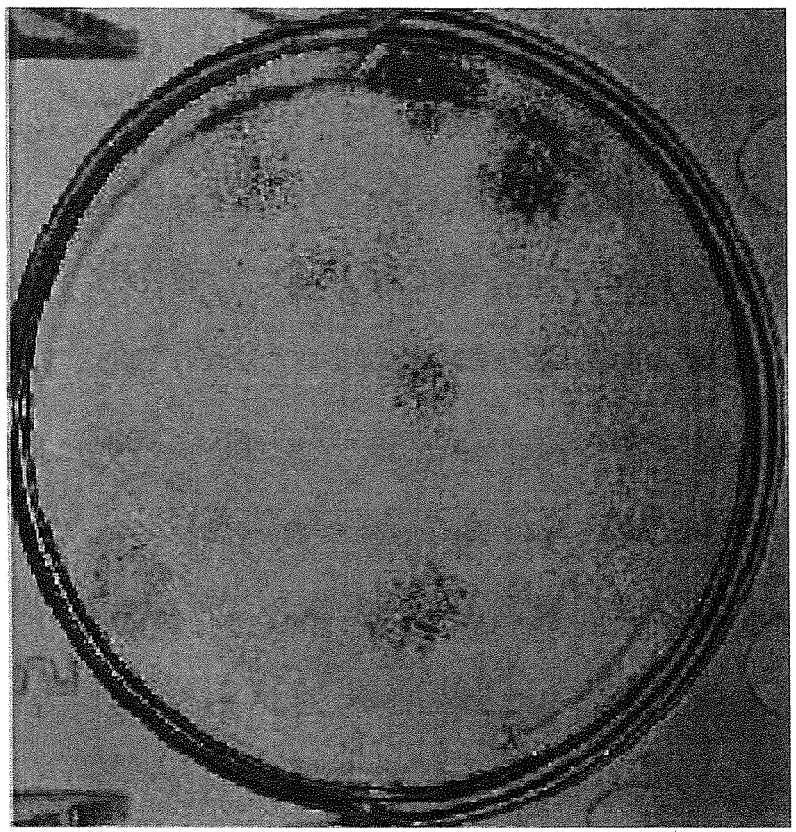
Figure 4:
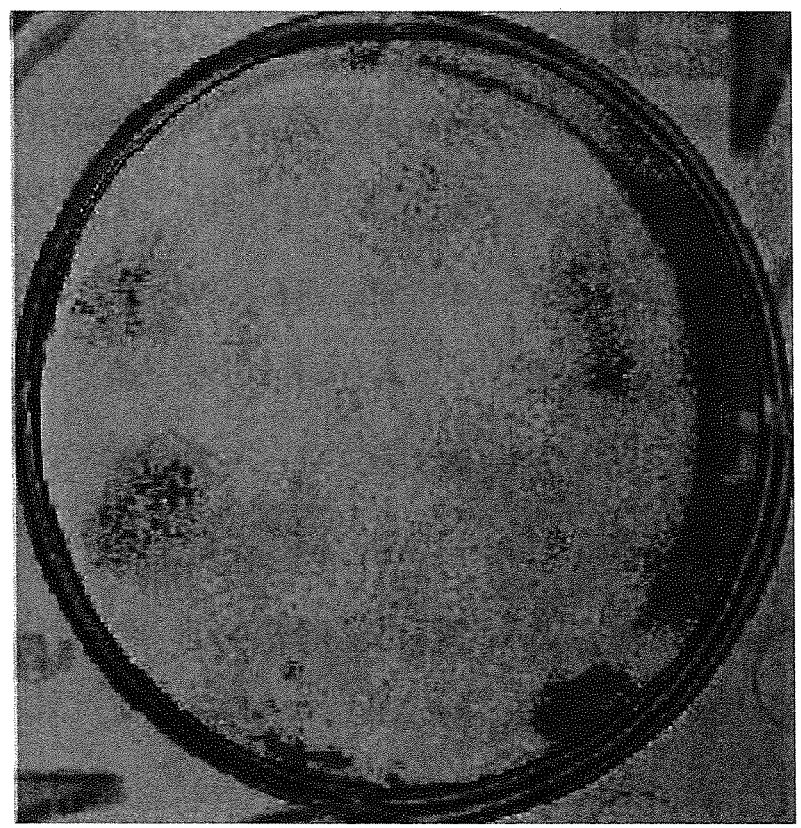

FIG. 4 provides images which compare colony forming ability of hMSCs cultured in a particular embodiment of the inventive serum-free medium to hMSCs cultured in conventional medium containing 10% FBS.

Figure 5:
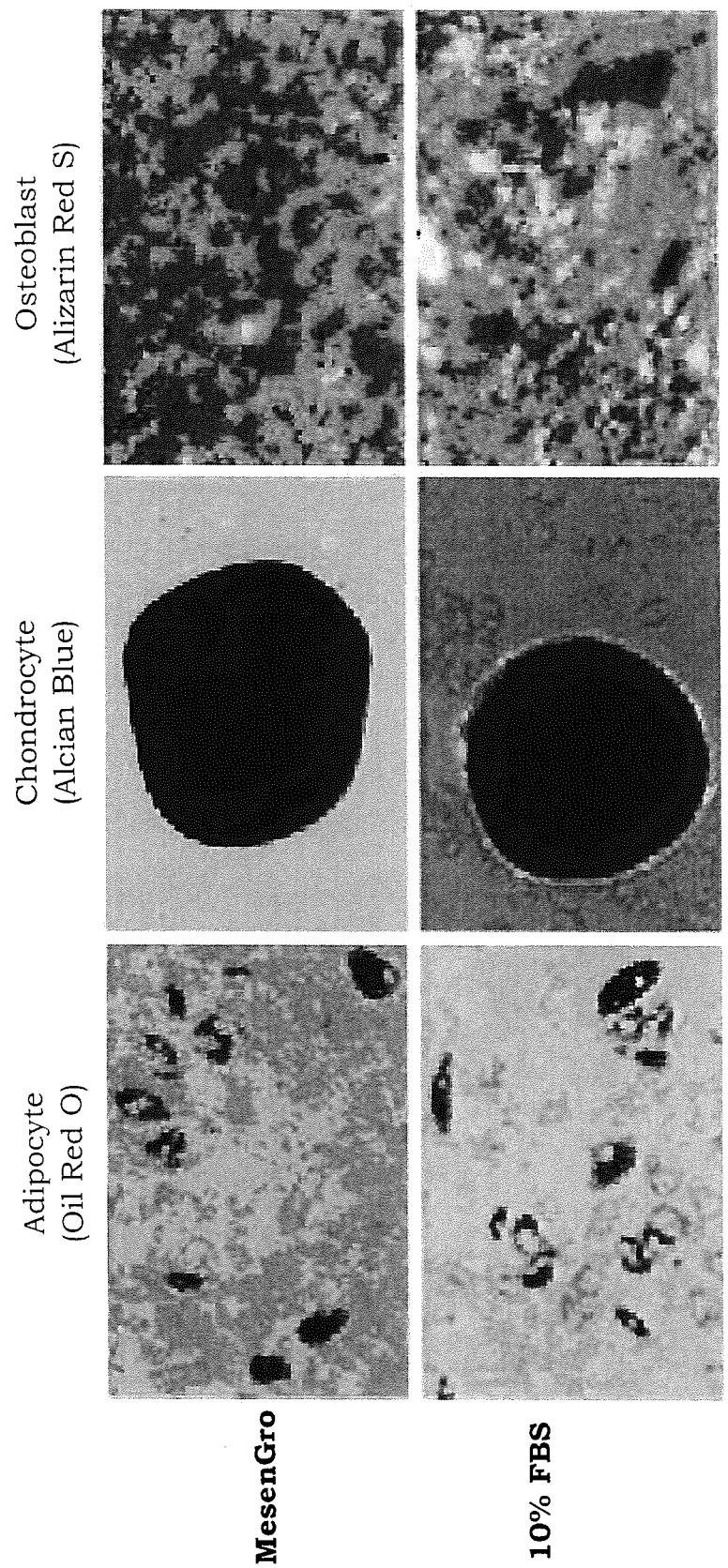

FIG. 5 provides images which compare multilineage differentiation potential of hMSCs after long term culture in a particular embodiment of the inventive serum-free medium to hMSCs cultured in conventional medium containing 10% FBS.

Figure 6:
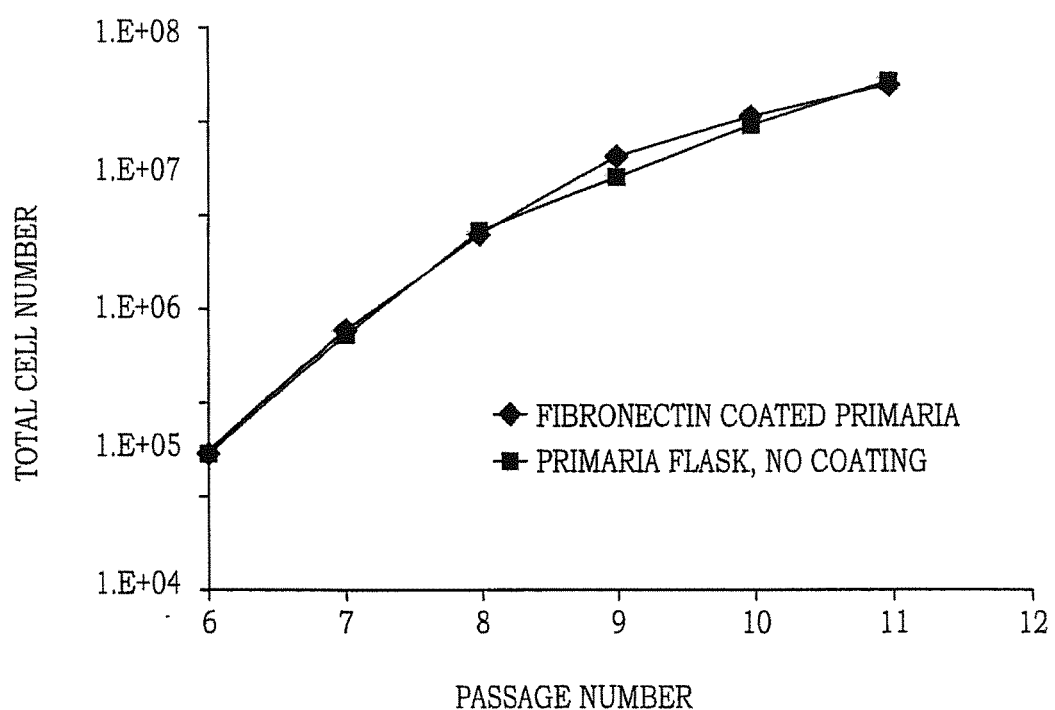

FIG. 6 is a graph of cell number over passage number which shows growth rates of hMSCs in a particular embodiment of the inventive serum-free medium are similar with or without use of a plate-coating on culture vessels.

Figure 7:
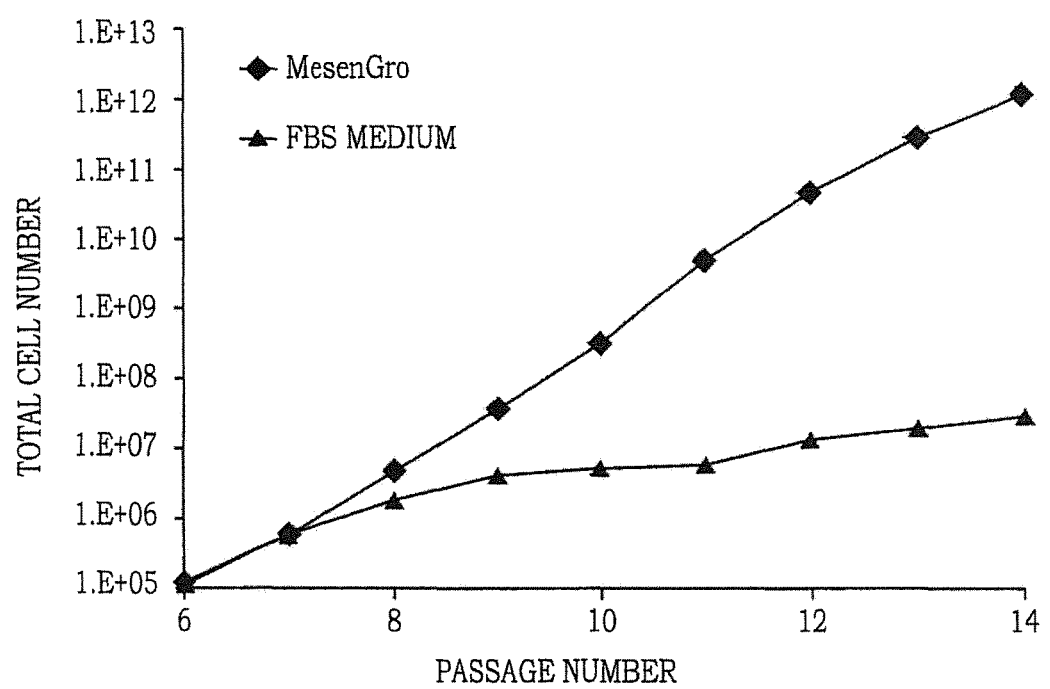

FIG. 7 is a graph of cell number over passage number which compares growth rate of umbilical cord blood derived MSCs cultured in an embodiment of a base medium supplemented with 10% FBS, L-glutamine, and penicillin streptomycin, to umbilical cord blood derived MSCs cultured in a particular embodiment of the inventive serum-free medium.

Figure 8:
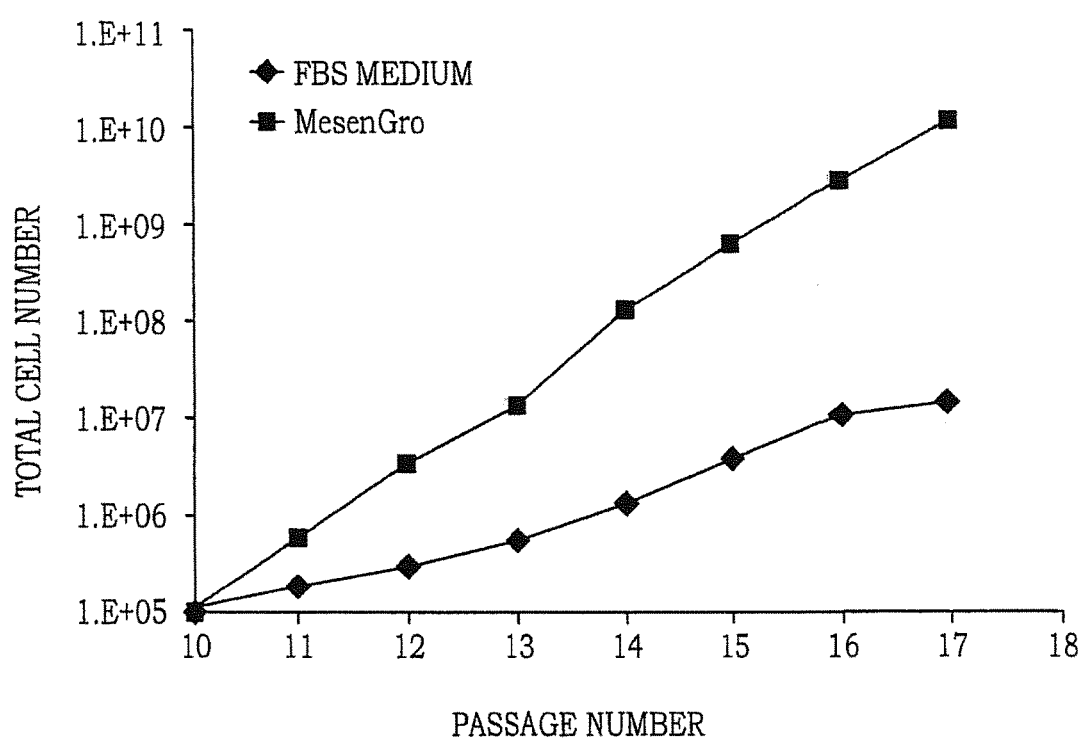

FIG. 8 is a graph of cell number over passage number which compares growth rate of adipose tissue derived MSCs cultured in the base medium supplemented with 10% FBS, L-glutamine, and penicillin streptomycin, to adipose tissue derived MSCs cultured in a particular embodiment of the inventive serum-free medium.

Figure 9:
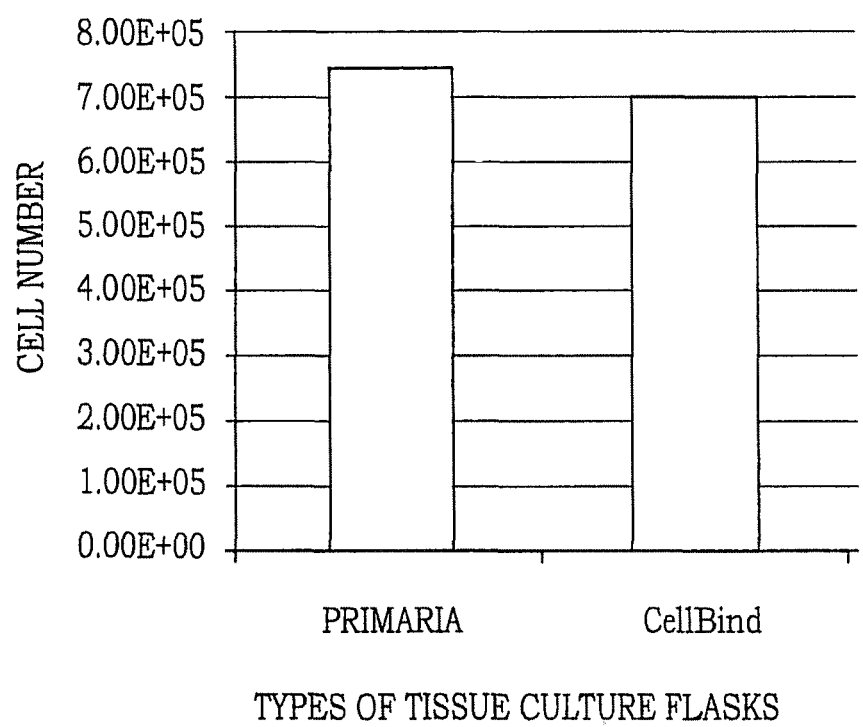

FIG. 9 is a bar graph of total cell numbers over the type of culturing flask utilized in culturing hMSCs in a particular embodiment of the inventive serum-free medium.

V. MODE(S) FOR CARRYING OUT THE INVENTION

A serum-free chemically defined cell culture media for the culture of cells. Specifically, a serum-free chemically defined cell culture medium for the culture of mesenchymal stem cells which can be used for ex-vivo mononuclear cell expansion while maintaining a pluripotent phenotype in which chondrocytes and osteocytes can be derived from the mesenchymal stem cells. Methods of use of a serum-free chemically defined cell culture media for differentiation of chondrocytes and osteocytes from in-vitro expanded mesenchymal stem cell populations and for treatment of disorders of the bone and cartilage benefited by a population of the derived chondrocytes or osteocytes.

For the purposes of the present invention, the term "serum-free" means the absence of any blood serum of any species including, but not limited to, the absence of fetal bovine serum, calf bovine serum, human serum, or the like, or combinations thereof.

For the purposes of the present invention, all numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

For the purposes of the present invention, the terms "combination" or "combining" refer to any method of putting two or more materials together. Such methods include, but are not limited to, mixing, blending, commingling, concocting, homogenizing, incorporating, intermingling, stirring, or the like.

For the purposes of the present invention, the term "a" or "an" entity refers to one or more of that entity; for example, "a protein" or "a peptide" refers to one or more of those compounds or at least one compound. As such, the terms "a" or "an", "one or more" and "at least one" can be used interchangeably herein. Furthermore, a compound "selected from the group consisting of" refers to one or more of the compounds in the list that follows, including combinations of two or more of the compounds. According to the present invention, an isolated compound is a compound that has been removed from its natural milieu. As such, "isolated" does not necessarily reflect the extent to which the compound has been purified. An isolated compound of the present invention can be obtained from its natural source, can be produced using molecular biology techniques or can be produced by chemical synthesis.

Additionally, while certain sources for particular components or elements of embodiments of the invention and specific product numbers for the components or elements are described; the invention is not so limited, and the same, equivalent or substantially similar components or elements suitable for use in embodiments of the invention can be obtained from a numerous and wide variety of sources.

Embodiments of the inventive medium including the best mode of the invention can provide a serum-free base medium (also referred to as the "base medium"). The serum-free base medium can include a mixture of Dulbecco's Modified Eagle Medium or a medium of the same, equivalent, or substantially similar composition (herein after referred to as "DMEM") (a suitable DMEM for use in embodiments of the invention can be obtained from Invitrogen, 5791 Van Allen Way, Carlsbad, Calif., in liquid form PN 11965 or as a powder as PN 12100 and prepared in accordance with the manufacturer's instructions) and MCDB201 medium or a medium of the same, equivalent, or substantially similar composition (hereinafter referred to as "MCDB") (a suitable MCDB for use in embodiments of the invention can be obtained from Sigma-Aldrich PN M6770). Each of these conventional media also available with certain added components such as glutamine, sodium pyruvate, HEPES, phenol red, glucose, and without certain components such as methionine, cystine, or calcium, each such medium can be utilized in certain embodiments of the base medium depending on the application.

Particular embodiments of the base medium can include DMEM and MCDB combined in a ratio of DMEM:MCDB (v/v) in the range of about 0.75:1.25 to about 1.25:0.75; however, the invention is not so limited, and embodiments which confer advantages in particular applications can be prepared using ratios of DMEM:MCDB within a range selected from the group including: about 0.75:1.25 and about 0.85:1.15, about 0.80:1.20 and about 0.90:1.10, about 0.85:1.15 and about 0.95:1.05, about 90:110 and about 1.05:0.95, about 1.00:1.00 and about 1.10:0.90, about 1.05:0.95 and about 1.15:0.85, about 1.10:0.90 and about 1.20:0.80, and about 1.15:0.85 and about 1.25:0.75. With respect to particular embodiments of the invention for the culture of mesenchymal stem cells ("MSCs") and in particular human mesenchymal stem cells ("hMSCs") a ratio of DMEM:MCDB of about 1:1 v/v can be utilized with suitable results.

Embodiments of the base medium can further include one or more of the components further described below which can be combined with the combination of DMEM and MCDB in various permutations, combinations, concentrations or amounts, depending upon the application. In each case, the one or more components can be used within the range or in the amounts described and depending upon the application or combination of components certain advantages can be achieved using a selected portion of the ranges described for any particular component or element.

Embodiments of the base medium can further include a buffer such as an amount of sodium bicarbonate in the range of about 3.2 g/L and about 4.2 g/L of the base medium and as to particular embodiments about 3.7 g/L. The pH of the base medium can be adjusted to a final pH in the range of about 7.3 to about 7.5 with an amount of sodium hydroxide with particular embodiments having a pH of about 7.4.

Embodiments of the base medium can further include a regulated iron source which releases an amount of iron upon binding with receptors of the cells being cultured. A non-limiting example of a regulated iron source can be an amount of transferrin having a concentration in said base medium in the range of about 2 mg/L and about 10 mg/L. As to particular embodiments of the base medium, the amount of transferrin can be selected from the group including: about 2 mg/L and about 4 mg/L, about 3 mg/L and about 5 mg/L, about 4 mg/L and about 6 mg/L, about 5 mg/L and about 7 mg/L, about 6 mg/L and about 8 mg/L, about 7 mg/L and about 9 mg/L, and about 8 mg/L and about 10 mg/L. Particular embodiments of the base medium can include an amount of transferrin of about 5 mg/L.

Embodiments of the base medium can further include an electron transport activator. The electron transport activator can comprise an amount of selenium or an amount of selenous acid; however, the invention is not so limited and other trace elements, metalloenzymes or proteins can be utilized to support electron transport. As to those embodiments which include an amount of selenous acid in the base medium, the amount can be in a range of about 0.0000025 g/L and about 0.0000050 g/L with a particular embodiment including about 0.0000037 g/L.

Embodiments of the base medium can further include one or more antioxidants. The antioxidants can include as non-limiting examples an amount of α-tocopherol acetate or an amount of ascorbic acid-2 phosphate, or an amount of both. Particular embodiments can include an amount of α-tocopherol acetate in the range of about 0.0001 g/L and about 0.0003 g/L and an amount of ascorbic acid-2 phosphate in the range of about 0.02 g/L and about 0.04 g/L. One non-limiting example includes an amount of α-tocopherol acetate of about 0.0002 g/L and an amount of ascorbic acid-2 phosphate of about 0.0322 g/L.

Embodiments of the base medium can further include one or more steroids. The steroids can include as non-limiting examples an amount of dexamethasone or an amount of hydrocortisone, or an amount of both. Particular embodiments can include an amount of dexamethasone in the range of about 2.0 µg/L and about 5.0 µg/L in combination with an amount of hydrocortisone of about 0.5 mg/mL and about 1.5 mg/mL. One non-limiting example of the base medium includes an amount of dexamethasone of about 0.000004 g/L in combination with an amount of hydrocortisone of about 0.001 g/L.

Embodiments of the base medium can further include an amount of 5-hydroxytryptamine in the range of about 0.001 g/L and about 0.003 g/L. One non-limiting example of the base medium includes an amount of 5-hydroxytryptamine of about 0.002 g/L.

Embodiments of the base medium can further include an amount of human serum albumin ("HSA")(which can be a recombinant human serum albumin ("rHSA")). Particular embodiments can include an amount of HSA in a range of about 0.1 g/L and about 0.3 g/L. One non-limiting example of the base medium includes an amount of HSA of about 0.25 g/L.

A particular non-limiting embodiment of the base medium for the culture of MSCs or hMSCs can comprise, consist essentially of, or consist of the combination of ingredients each in the final concentration set out in Table 1.

TABLE 1

Medium for MSC Culture.

| Ingredient | Final Concentration |
| --- | --- |
| MCDB201 | 0.5 L/L |
| DMEM | 0.5 L/L |
| sodium bicarbonate | 3.7 g/L DMEM |
| NaOH for 1 L Mix | final pH = 7.39 |
| rHSA | 0.25 g/L |
| transferrin | 0.005 g/L |
| selenous acid | 0.0000037 g/L |
| ascorbic acid-2 phosphate | 0.032205 g/L |
| 5-Hydroxytryptamine | 0.002127 g/L |
| dexamethasone | 0.000003925 g/L |
| hydrocortisone | 0.001 g/L |
| α-Tocopherol acetate | 0.0002 g/L |

Understandably, this particular embodiment of the base medium is not intended to be limiting but rather exemplary of the numerous and varied embodiments which can be prepared using equivalent or substantially similar components, adjusted in concentration based upon the particular cells, cell lines, MSCs, or hMSCs being cultured. The final concentrations listed for the embodiment of Table 1 may vary from the absolute value in a range related to the normal variations in production, depending upon the particular application, useful in culturing MSCs or hMSC. Additionally, certain embodiments of the invention may include fewer components than are listed in Table 1 and these embodiments are intended to be encompassed by the breadth of the invention.

Embodiments of the invention can further include a base medium supplement which can be combined with the base medium (the combination also referred to as the "supplemented medium"). The base medium supplement can include one or more cell growth factors, one or more phospholipid growth factors, and one or more WNT signaling pathway activators, in various permutations and combinations. Understandably, embodiments of the inventive serum-free medium do not have to, but can include, the one or more of the cell growth factors, the one or more phospholipid growth factors, or the one or more WNT signaling pathway activators, in various combinations and permutations depending upon the application.

Accordingly, embodiments of the base medium supplement can include the one or more cell growth factors such as: insulin which can be obtained from Sigma-Aldrich PN 16634 (CAS NO.: 11070-73-8), basic fibroblast growth factor human (bFGF) which can be obtained from Sigma-Aldrich PN F0291-25UG (CAS No.: 106096-93-9), Platelet-Derived Growth Factor bb (PDGF-bb) which can be obtained from Sigma-Aldrich PN P3201, Epiderman Growth Factor (EGF) which can be obtained from Sigma-Aldrich PN E9644 (CAS NO.: 62253-63-8), and Insulin Like Growth Factor-1 (IGF-1) (CAS NO.: 7733-29-1) which can be obtained from Sigma-Aldrich PN I8779 or PN I3769.

Embodiments of the base medium supplement can include an amount of insulin. Particular embodiments can have a concentration in the serum-free medium in the range of about 0.004 g/L and about 0.006 g/L. One non-limiting example includes an amount of insulin of about 0.005 g/L.

Embodiments of the base medium supplement can include an amount of bFGF. Particular embodiments can have a concentration of bFGF in the serum-free medium in the range of about 5 ng/mL and about 20 ng/mL. One non-limiting example includes an amount of bFGF of about 10 ng/mL.

Embodiments of the base medium supplement can include an amount of PDGF-bb. Particular embodiments can have a concentration of PDGF-bb in the serum-free medium in the range of about 5 ng/mL and about 20 ng/mL. One non-limiting example includes an amount of PDGF-bb in the serum-free medium of about 10 ng/mL.

Embodiments of the base medium supplement can include an amount of EGF. Particular embodiments can have a concentration of EGF in the serum-free medium in the range of about 15 ng/mL and about 25 ng/mL. One non-limiting example includes an amount EGF in the serum-free medium of about 20 ng/mL.

Embodiments of the base medium supplement can include an amount of IGF-1. Particular embodiments can have a concentration of IGF-1 in the serum-free medium in the range of about 2 ng/mL and about 10 ng/mL. One non-limiting example includes an amount IGF-1 in the serum-free medium of about 5 ng/mL.

As to each of the above-described cell growth factors: PDGF-bb, bFGF, EGF, and IGF-1, there can be advantages to concentrations in the serum-free medium selected from the group including: about 2 ng/mL to about 4 ng/mL, about 3 ng/mL to about 5 ng/mL, about 4 ng/mL to about 6 ng/mL, about 5 ng/mL to about 7 ng/mL, about 6 ng/mL to about 8 ng/mL, about 7 ng/mL to about 9 ng/mL, about 8 ng/mL to about 10 ng/mL, about 9 ng/mL to about 11 ng/mL, about 10 ng/mL to about 12 ng/mL, about 11 ng/mL to about 13 ng/mL, about 12 ng/mL to about 14 ng/mL, about 13 ng/mL to about 15 ng/mL, about 14 ng/mL to about 16 ng/mL, about 15 ng/mL to about 17 ng/mL, about 16 ng/mL to about 18 ng/mL, about 18 ng/mL to about 20 ng/mL, and about 19 ng/mL to about 20 ng/mL.

Embodiments of the base medium supplement can include one or more phospholipid growth factors, such as: lysophosphatidic acid ("LPA")(CAS NO.: 22022-87-5) which can be obtained from Sigma-Aldrich PN L7260, and sphingosine 1-phosphate ("S1P")(CAS NO.: 26993-30-6) which can be obtained from Sigma-Aldrich PN S9666. Particular embodiments can have a concentration of each of LPA or S1P, or of both, in the serum-free medium in the range of about 80 nM and about 200 nM. One non-limiting example includes an amount LPA in the serum-free medium of about 100 nM combined with an amount of S1P in the serum-free medium of about 150 nM.

As to each of the above-described phospholipid growth factors there can be advantages to concentrations in the serum-free medium selected from the group including: about 80 nM and about 100 nM, about 90 nM and about 110 nM, about 100 nM and about 120 nM, about 110 nM and about 130 nM, about 120 nM and about 140 nM, about 130 nM and about 150 nM, about 140 nM and about 160 nM, about 150 nM and about 170 nM, about 160 nM and about 180 nM, about 190 nM and about 200 nM.

Embodiments of the base medium supplement can include one or more WNT signaling pathway activators. The WNT signaling pathway activators can be selected from the non-limiting group including: a human WNT-3a protein ("WNT3A") which can be obtained from StemRD Inc., Burlingame, Calif. PN W3A-H005 and R-spondin-1 ("RSPO1") which can be obtained from StemRD Inc., Burlingame, Calif. PN RSPO-005. Particular embodiments can include each of the one or more WNT signaling pathway activators in a concentration in the serum-free medium in a range of about 10 ng/mL and about 50 ng/mL. One non-limiting example includes an amount WNT3A in the serum-free medium of about 20 ng/mL combined with an amount of RSPO1 in the serum-free medium of about 40 ng/mL.

A particular non-limiting embodiment of the base medium supplement for the culture of MSCs or hMSCs can comprise, consist essentially of, or consist of the combination of ingredients each in the final concentration in the serum-free medium set out in Table 2.

TABLE 2

Chemically Defined MSC Medium Growth Factors.

| Growth Factor | Final Concentration |
| --- | --- |
| insulin | 0.005 g/L |
| PDGF-bb | 10 ng/mL |
| bFGF | 10 ng/mL |
| EGF | 20 ng/mL |
| IGF-1 | 5 ng/mL |
| LPA | 100 nM |
| S1P | 150 nM |
| WNT3A | 20 ng/mL |
| RSPO1 | 40 ng/mL |

Again, while Table 2 lists the final concentration of the various cell growth factors, lipid growth factors, and WNT signaling pathway activators utilized in a particular embodiment of the inventive serum-free medium for the expansion of MSCs in culture; the invention is not so limited, and additional embodiments of the invention can be achieved for the culture of cells including, but not limited to, deriving chondrocytes and osteocytes from MSCs or hMSCs, using one or more than one, or all of the growth factors listed in the table in various combinations and permutations with the concentration of each component or element varied as above described depending upon the application.

Embodiments of the serum-free medium can further include an amount of transforming growth factor beta 1 ("TGFB1") which can be obtained from StemRD Inc., Burlingame, Calif. PN TGF-b-005. The amount of TGFB1 can be an amount sufficient to derive chondrocytes from mesenchymal stem cells cultured in the serum-free chemically defined cell culture medium above described. Particular embodiments of the serum-free medium can include a concentration of TGFB1 in the serum-free medium in the range of about 0.5 ng/mL and about 5 ng/mL. One non-limiting example includes an amount TGFB1 having a concentration in the serum-free medium of about 1 ng/mL.

Embodiments of the serum-free medium can further include an amount of bone morphogenic protein 2 ("BMP2") which can be obtained from Sigma-Aldrich PN B3555. The amount of BMP2 can be an amount sufficient to derive osteocytes from mesenchymal stem cells cultured in the serum-free chemically defined cell culture medium above described. Particular embodiments of the serum-free medium can include a concentration of BMP2 in the serum-free medium in the range of about 0.5 ng/mL and about 5 ng/mL. One non-limiting example includes an amount TGFB1 having a concentration in the serum-free medium of about 1 ng/mL.

Understandably, embodiments can include one or both of the TGFB1 or BMP2 sufficient to derive a population of chondrocytes or a population of osteocytes or a population including both a population chondrocytes and a population of osteocytes from the MSCs or hMSCs. A particular embodiment of the serum-free medium suitable for deriving chondrocytes or osteocytes from hMSCs can comprise, consist essentially of, or consist of a combination of the ingredients enumerated in Table 1 and Table 2 and then admixing an amount of either of or both of TGFB1 and BMP2 into the combination.

The following working examples are intended to be illustrative of methods of making and using the inventive serum-free chemically defined cell culture media (including certain embodiments of the inventive base media and the inventive supplemented media) sufficient for the person of ordinary skill in the art to make and use the broad range of embodiments encompassed by the invention.

Example 1. Recovery of Cryopreserved Cells

Frozen cells including, but not limited to MSCs, and in particular hMSCs, can be adapted to the inventive serum-free medium above-described, regardless of the medium prior used to grow or freeze cells. The stepwise procedure includes thawing frozen cells, such as hMSCs, in a water bath at about 37° C. The hMSCs can be transferred into a 50 mL conical tube or other suitable vessel. For each 1 mL of hMSC suspension, add drop-wise about 10 mL of the inventive serum-free medium pre-warmed to about 37° C. while gently swirling. Transfer the contents of the conical tube into a tissue culture flask or plated multiple wells of a tissue culture plate. Alternatively, hMSCs can also be centrifuged at about 250×g (~1200 rpm) for about 10 minutes, re-suspended in the inventive serum-free medium (the base medium or the supplemented medium depending on the application) and then transferred or plated. The hMSCs can be incubate at about 36° C. to about 38° C. in a humidified atmosphere containing about 4% to about 6% carbon dioxide. After about 24 hours, replace the inventive serum-free medium in which the hMSCs were transferred or plated with fresh inventive serum-free medium. Maintain the hMSC cell culture by changing the inventive serum-free medium every 2 days until cell expansion requires passaging or splitting.

Example 2. Passaging of Cells

Coating or other treatment to the surface of cell culture vessels may not be necessary when culturing cells, including, but not limited to MSCs and in particular human MSCs in embodiments of the inventive serum-free medium (such as the "base medium" or the "supplemented medium"). Sufficient and typically optimal cell attachment and growth of cells including MSCs and hMSCs can be achieved utilizing conventional tissue culture vessels without coating. As a non-limiting example, negatively charged polystyrene vessels, such as 25 cm$^2$ tissue culture flask available through BD Primaria, 1 Becton Drive, Franklin Lakes, N.J. (BD Cat#353808) and BD Primaria, Falcon 6-well plates (BD Cat#353046) for cell passage can be utilized with embodiments of the inventive medium without plate-coating; however, the invention is not so limited, and if desired the surface of the vessels can be coated with Fibronectin at about 0.5-1.0 microgram/cm$^2$ surface area for about 1 hour at about 37° C., followed by plating of cells in the inventive serum-free medium. Cells, including MSCs and hMSCs cultured in serum-containing or serum-free media can be quickly and easily adapted into embodiments of the inventive serum-free medium. In most cases, a one-step transition from serum-containing medium into embodiments of the inventive serum-free medium can be sufficient. If so desired, step-wise adaptation with a gradual increase of the amount of the inventive serum-free medium (e.g. 25%, 50%, etc) can also be performed, as follows.

Visually inspect the stock culture of cells (whether grown in the inventive serum-free medium or other medium) under the microscope and confirm that the cells are ready to be sub-passaged. To maintain the growth potential of MSCs, cells can be passaged when they reach about 70% confluency. If the MSC or hMSC culture reaches confluency of about 80% or higher, the cells may stop proliferating after passage. Therefore, MSCs and hMSCs can be passaged prior to reaching confluency of 80% to avoid this result. Add about 0.05% Trypsin/EDTA solution or TrypLE™ Express to the vessel, tilt vessel to cover all the cells at room temperature.

Observe the MSC or hMSC or cells under a microscope. When cells start to detach, gently tap the side of the vessel to help loosen the remaining cells. The time required for the cells to detach should be about 1 minute to about 3 minutes, if the MSCs or hMSCs have been cultured in embodiments of the inventive serum-free medium. Interestingly, cells grown in conventional serum-containing media may require a longer incubation time to detach.

Once the cells have detached, proceed to the following step. Do not leave MSCs in cell dissociation enzyme, such as Trypsin or TrypLE™ Express, for an extended amount of time after the cells have detached, as this will adversely affect the growth of MSCs.

Upon cell detachment, add sufficient Dulbeccos Phosphate Buffered Saline ("DPBS") to cover the surface area (a DPBS suitable for use in the inventive method available from Sigma-Aldrich, St. Louis, Mo. as Product No. D4031). Collect the cell suspension in a sterile 15 mL conical tube. Break cell clumps by tapping flask firmly or pipet the suspension, if necessary.

Centrifuge cells at 1200 rpm (250×g) for 10 minutes. Aspire and discard substantially all the supernatant. Resuspend cells in DPBS or the inventive serum-free medium, and centrifugate again. Aspire the supernatant and resuspend cells in pre-warmed inventive medium. Take an aliquot from the cell suspension for cell counting:

Transfer cells into tissue culture vessels at a density of about 3.6×10$^3$ cells/cm$^2$. Tilt the vessel a few times to ensure even distribution of cell suspension. Incubate at 36 to 38° C. in a humidified atmosphere of 4 to 6% $CO_2$. Replace culture medium every 2 days with fresh, pre-warmed inventive medium. Pass cells when cell confluency reaches about 70% (typically at 3 day intervals).

Example 3. Cryopreservation of Cells

Prepare cryopreservation solution by admixing the base medium with about 10% supplemented medium and 10% Dimethyl Sulfoxide (DMSO). Pellet cells, such as MSCs, by centrifugation, gently re-suspend cells in cryopreservation solution to about 1.0×10$^6$ cells/mL, and transfer to cryovials. Place cryovials in a freezing container (such as a Nalgene, 5100 Cryo Freezing Container Product No 5100-0001) and place in a −70° C. freezer overnight. Transfer cryovials to liquid nitrogen for long-term storage.

Example 4. Chondrogenesis of Cells

The differentiation potential of cells such as MSCs or hMSCs expanded in the inventive serum-fee medium can be tested in-vitro. The expanded cells may be induced to form chondrocytes under the experimental conditions described.

The expanded MSCs can be transferred in anchorage-independent conditions and maintained as a pellet culture for about 1 to about 4 weeks in the inventive serum free base medium otherwise using the method previously described by Johnstone et al., Exp. Cell Res. 238, 265-272 (1998) to induce chondrogenesis of MSCs expanded in the inventive serum-free.

Results indicate that the MSCs expanded in embodiments of the inventive serum-free base medium formed a cartilaginous structure, which can stain positive for alcian blue and type II collagen, and can stain mostly negative for type I collagen. The extent of chondrogenesis may be enhanced by the addition of TGFB1 and WNT pathway inhibitors to the inventive base medium, or use of the supplemented medium, above described.

The results evidence that certain embodiments of the inventive base medium, the inventive base medium further including TGFB1 and WNT pathway inhibitors, or the supplemented medium, may induce chondrogenesis to the same or greater extent, rate, or efficiency than conventional medium containing FBS.

Example 5. Osteogenesis of Mesenchymal Stem Cells

The differentiation potential of cells such as MSCs or hMSCs expanded in the inventive medium can be tested in-vitro. The expanded cells may be induced to form osteocytes under the experimental conditions described.

Results evidence that cells such as MSCs expanded in the inventive base medium formed a bone structure, which can stain positive for Alizarin Red S. The extent of osteogenesis may be enhanced by the addition of BMP2 and WNT pathway activators to embodiments of the inventive base medium or by use of the supplemented medium, as above described.

The results may evidence that methods which utilize the inventive base medium, the base medium, or the supplemented medium, may induce osteogenesis at the same or greater extent, rate, or efficiency than conventional medium containing FBS.

Example 6. Results

Figure 1:
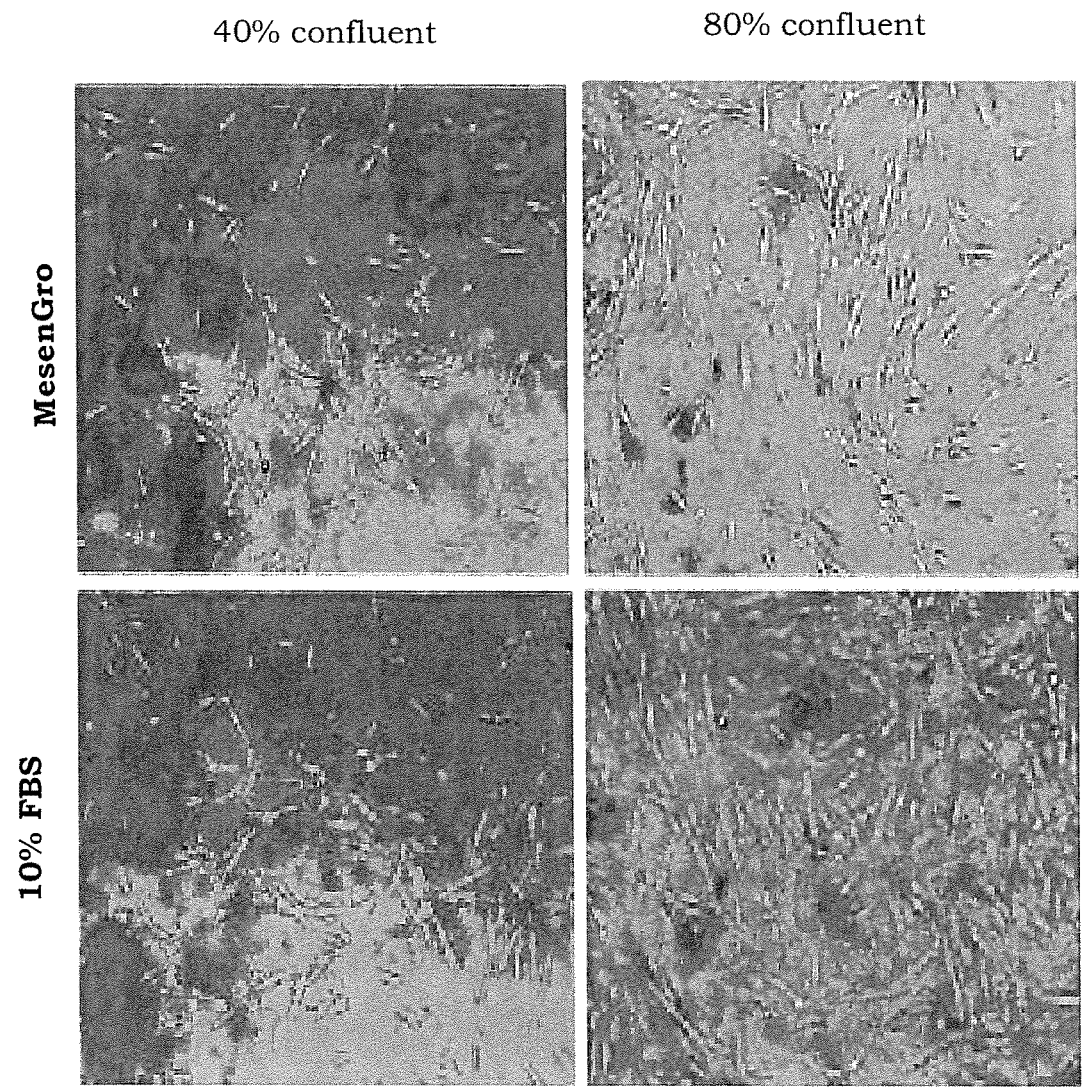

Now referring primarily to FIG. 1, which provides images that compare cell cultures of hMSCs grown in conventional medium containing 10% FBS and cell cultures of hMSCs grown in the inventive serum-free medium (also referred to in the Figures as "MesenGro") at each of 40% confluence and at 80% confluence. The comparison of the images evidences that hMSC cultures in the inventive serum-free medium do not appear substantively different than hMSC cultures in conventional medium containing 10% FBS. The inventive serum-free medium provides the advantage of not having to utilize FBS which can vary to a greater degree in composition, and cannot be traced back to the donor animal, and may inhibit or prevent MSC or hMSC differentiation. The inventive serum-free medium can afford other advantages as further described below.

Figure 2:
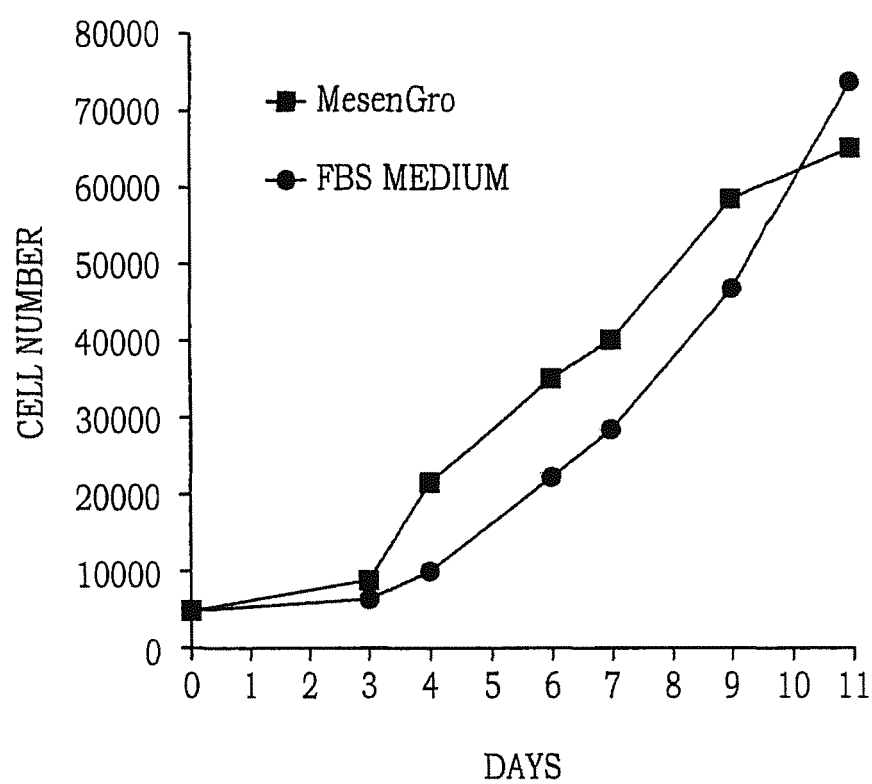
FIG. 2 is a graph of cell number over days which compares the growth rate of hMSCs cultured in conventional medium containing 10% FBS and the growth rate of hMSCs cultured in a particular embodiment of the inventive serum-free medium.

Now referring primarily to FIG. 2, a graph of cell number over time in days compares cell growth of hMSCs in conventional medium containing 10% FBS to cell growth in the inventive serum-free medium ("MesenGro"). Cell numbers per well (24-well plate) at each time point were counted with a medium change every 2 days. Surprisingly, the graph evidences that the rate of cell growth of hMSCs in the inventive serum-free medium can be greater than in conventional medium containing 10% FBS. In certain applications this affords the advantage of allowing passage at an earlier point in time or afford the advantage of obtaining a desired number of cells in a lesser amount of time.

Figure 3:
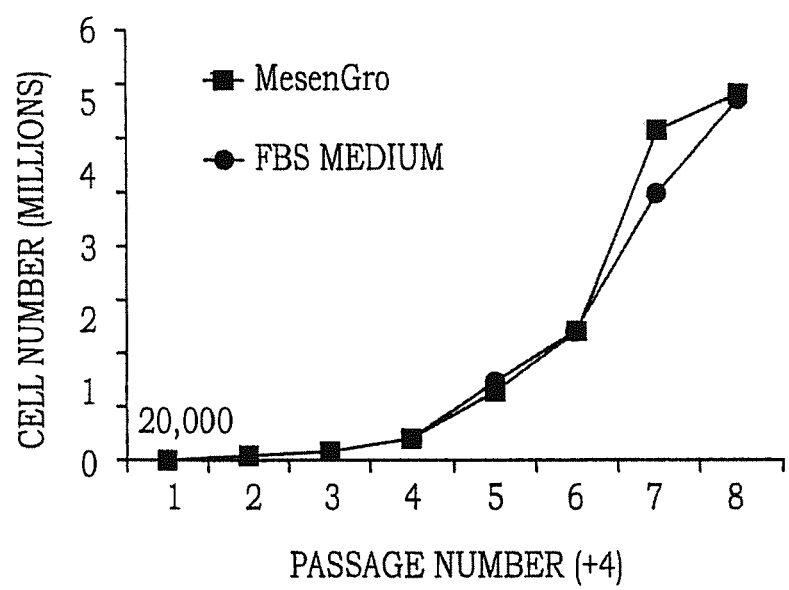
FIG. 3 is a graph of cell number over passage number which compares total number of hMSCs at each split where the starting passage number is 4 from conventional medium containing 10% FBS into either a particular embodiment of the inventive serum-free medium or in conventional medium containing 10% FBS.

Now referring primarily to FIG. 3, a graph of total hMSC numbers over passage number compares cell growth of hMSCs in conventional medium containing 10% FBS to cell growth in the inventive serum-free medium (referred to as "MesenGro"). Total cell numbers per well (6-well plate) at each split (every 3 days) were counted. The starting passage number is 4 (from conventional medium containing 10% FBS into either the inventive serum-free medium or into conventional medium containing 10% FBS), with an initial cell density of about 20,000/well. The graph evidences a similar exponential expansion of hMSC in the inventive serum-free medium as in the conventional medium.

Now referring primarily to FIG. 4, which provides images of the colony forming ability of hMSCs grown in conventional medium containing 10% FBS as compared with the colony forming ability of hMSCs grown in the inventive serum-free medium (referred to as "MesenGro"). The images evidence no substantive difference in the colony forming ability of those hMSCs grown in the inventive serum-free medium as compared to those hMSCs grown in conventional medium containing 10% FBS.

Now referring primarily to FIG. 5, which provides images which compare the multilineage differentiation potential of hMSCs after long-term culture in the inventive serum-free medium (referred to as "MesenGro") to hMSCs after long-term culture in conventional medium containing 10% FBS. At passage 9, cells were plated in 6-well plate, and differentiation achieved in the inventive serum-free medium was compared to differentiation achieved in the conventional medium containing 10% FBS after 18-24 days. The results evidence that hMSCs cultured in the inventive serum-free medium retain a multilineage differentiation potential comparable and which may be greater than hMSCs cultured in conventional medium containing 10% FBS.

Now referring primarily to FIG. 6, which is a graph of cell number over passage number. Growth rates of bone marrow derived hMSCs (Cellular Engineering Technologies) in the inventive serum-free medium are similar on BD Primaria Falcon 6-well plates (BD Cat#353046) with or without use of a fibronectin coating as above described. This affords an advantage over several other commercially available serum-free media, such as StemPro MSC SFM from Invitrogen (PN A10332-01) and MesenCult-XF from StemCell Technologies (PN 05420), which requires the step of plate-coating to achieve similar cell number over passage number results.

Now referring primarily to FIG. 7, which is a graph of cell number over passage number which compares growth rate of umbilical cord blood derived MSCs (Cellular Engineering Technologies) cultured in an embodiment of the base medium supplemented with 10% FBS, L-glutamine, and penicillin streptomycin to umbilical cord blood derived MSCs cultured in an embodiment of the inventive serum-free medium (referred to as "MesenGro").

Umbilical cord blood derived MSCs were cultured for two to six passages in medium containing 10% FBS. Cultured MSCs were then split into two groups and each of the two groups cultured in either of: the base medium supplemented with 10% FBS, L-glutamine, and penicillin streptomycin, or the inventive serum-free medium (referred to as "MesenGro").

Both groups were cultured on BD Primaria T25 flasks, and were passed every 3 to 4 days. Seeding density was $1.25 \times 10^5$ cells per flask at each passage. Growth rates in total cell numbers of umbilical cord-blood derived MSCs in the inventive serum-free medium (referred to as "MesenGro") was substantially greater than in the base medium supplemented with 10% FBS, L-glutamine, and penicillin streptomycin.

Now referring primarily to FIG. 8, which is a graph of cell number over passage number which compares growth rate of adipose tissue derived MSCs (Cellular Engineering Technologies) cultured in an embodiment of the base medium supplemented with 10% FBS, L-glutamine, and penicillin streptomycin to adipose tissue derived MSCs cultured in an embodiment of the inventive serum-free medium (referred to as "MesenGro").

Adipose tissue derived MSCs were cultured for two to six passages in medium containing 10% FBS. Cultured MSCs were then split into two groups and each of the two groups cultured in either of: the base medium supplemented with 10% FBS, L-glutamine, and penicillin streptomycin, or the inventive serum-free medium (referred to as "MesenGro").

Both groups were cultured on BD Primaria T25 flasks, and were passed every 3 to 4 days. Seeding density was $1.25 \times 10^5$ cells per flask at each passage. Growth rates in total cell numbers of adipose tissue derived MSCs in the inventive serum-free medium (referred to as "MesenGro") was substantially greater than in the base medium supplemented with 10% FBS, L-glutamine, and penicillin streptomycin.

Now referring primarily to FIG. 9, which provides a bar graph of total cell numbers over the type of culturing flask utilized in culturing hMSCs. Frozen bone marrow derived MSCs (Cellular Engineering Technologies) were thawed in accordance with the procedure of Example 1. Bone marrow derived MSCs that had been passed for 6 passages in the inventive serum-free medium ("MesenGro") on uncoated Primaria T25 flasks were then seeded at $0.09 \times 10^6$ per flask on to two different kinds of flasks: BD Primaria T25 and Corning CellBIND T25. Each different kind of flask was uncoated, and cells were all cultured in the inventive serum-free medium ("MesenGro"). After 4 days, cell numbers from each flask were counted. As between different kinds of uncoated culture flasks there was not substantial difference in the total number of MSCs. This evidences that the inventive serum-free medium can be used for the culturing of MSCs in a variety of different uncoated culturing flasks, each culture flask manufactured in accordance with a correspondingly different manufacturer's specification.

Advantages of Culturing MSCs in the Serum-Free Medium

The inventive serum-free medium confers a variety of advantages over culturing MSCs or hMSCs in a medium supplemented with fetal bovine serum or with human autologous serum, or other serum containing medium.

Firstly, embodiments of the inventive serum-free medium do not contain bovine serum, human serum, or other animal serum. Accordingly, the embodiments of the inventive serum-free medium cannot contain any corresponding blood born pathogens, such as viruses and mad cow prions, bovine spongiform encephalopathy ("BSE"), or the like.

Secondly, embodiments of the inventive serum-free medium do not invoke antibody generation to xenobiotic proteins which can invoke immune responses in patients into which populations of ex-vivo expanded populations of MSCs can be transferred to in treatment of disorders of the cartilage and bone.

Thirdly, embodiments of the inventive serum-free medium have a substantially lesser lot to lot variation in composition and thereby lot to lot performance of the inventive serum-free medium can be utilized with a greater consistency.

Fourthly, embodiments of the inventive serum-free medium can be utilized with uncoated culture flasks manufactured by a variety of different manufactures. By comparison, other commercially available serum-free media, such as Invitrogen's StemPro MSC SFM, or StemCell Technologies' MesenCult-XF, require pre-coating the culture flasks with attachment material.

Fifthly, embodiments of the inventive serum-free medium exhibit unexpectedly good results in supporting expansion of MSCs derived from a variety of MSC sources such as umbilical cord matrix, umbilical cord blood, bone morrow and adipose tissue-derived MSCs as compared to conventional medium supplemented with fetal bovine serum as evidenced by FIG. 7 and FIG. 8 and the above description.

Uses of MSCs Cultured in Embodiments of the Serum-Free Medium

A first non-limiting use of embodiments of the inventive serum-free medium can be provision of a cell culture kit which includes a portion of or all of the components of the inventive serum-free medium whether combined or combinable in various permutations and combinations to prepare various embodiments of the serum-free medium for the purpose of ex-vivo expansion of cells, MSC, or hMSC populations.

Additionally, in light of achieving ex-vivo expansion of MSC populations in general and in particular hMSC populations which may be further differentiated to produce chondrocytes or osteocytes in embodiments of the inventive serum-free medium with unexpectedly good results as above described, the use of such expanded or differentiated populations of MSCs to treat disorders that can benefited by the transfer of one or more of such expanded populations of MSCs, whether or not differentiated, is evident. As a non-limiting example, a population of mesenchymal stem cells expanded ex-vivo using the inventive serum-free medium can be obtained as above described. A therapeutically effective amount of the population of mesenchymal stem cells expanded as above described can be administered to an individual.

In certain instances, the individual may be suffering from a disorder of the cartilage tissue and a population of osteocytes derived from a population of mesenchymal stem cells expanded ex-vivo using the inventive serum-free medium can be obtained and a therapeutically effective or sufficient amount of such population of osteocytes can be administered to the individual to benefit, to assist in reconstituting, or reconstituting cartilage tissue.

In certain instances, the individual may be suffering from a disorder of the bone and a population of chondrocytes derived from a population of mesenchymal stem cells expanded ex-vivo using the inventive serum-free medium can be obtained and a therapeutically effective or sufficient amount of such population of chondrocytes can be administered to the individual to benefit, to assist in reconstituting or reconstituting bone.

As can be easily understood from the foregoing, the basic concepts of the present invention may be embodied in a variety of ways. The invention involves numerous and varied embodiments of a serum-free medium including the best mode useful in the ex-vivo expansion and differentiation of cells, MSCs and hMSCs and treatment of disorders benefitted by administration of populations of MSCs or differentiated populations derived from such MSCs.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of a "cell culture" should be understood to encompass disclosure of the act of "culturing cells"—whether explicitly discussed or not—and, conversely, were there effectively disclosure of the act of "culturing cells", such a disclosure should be understood to encompass disclosure of a "cell culture" and even a "means for culturing cells." Such alternative terms for each element or step are to be understood to be explicitly included in the description.

In addition, as to each term used it should be understood that unless its utilization in this application is inconsistent with such interpretation, common dictionary definitions should be understood to included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment.

Thus the applicant(s) should be understood to claim at least: i) a serum-free cell culture medium as herein disclosed and described, ii) the related methods disclosed and described, iii) similar, equivalent, and even implicit variations of each of these devices and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this international PCT patent specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

The claims set forth in this international PCT patent specification are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

We claim:

1. A serum-free chemically defined cell culture medium composition, the composition comprising:
   a serum free base medium comprising Dulbecco's Modified Eagle Medium and MCDB 201 medium;
   a regulated iron source;
   an electron transport activator;
   an antioxidant;
   a steroid;
   5-hydroxytryptamine;
   a human serum albumin;
   a phospholipid growth factor selected from lysophosphatidic acid and sphingosine 1-phosphate;
   a cell growth factor;
   human wingless/integrated 3a; and
   R-spondin-1, said composition adjusted to a pH in a range of about 7.3 to about 7.5.

2. The composition of claim 1, wherein said Dulbecco's Modified Eagle Medium and said MCDB 201 medium have a ratio in the range of about 0.75:1.25 v/v to about 1.25:0.75 v/v.

3. The composition of claim 2, wherein said ratio of Dulbecco's Modified Eagle Medium to MCDB201 medium is in a range selected from the group consisting of: about 0.75:1.25 to about 0.85:1.15, about 0.80:1.20 to about 0.90:1.10, about 0.85:1.15 to about 0.95:1.05, about 90:1.10 to about 1.05:0.95, about 1.00:1.00 to about 1.10:0.90, about 1.05:0.95, about 1.15:0.85, about 1.10:0.90 to about 1.20:0.80, and about 1.15:0.85 to about 1.25:0.75.

4. The composition of claim 3, wherein said steroid comprises dexamethasone and hydrocortisone wherein said dexamethasone has a concentration in a range of about 2.0 µg/mL to about 5.0 µg/mL, and wherein said hydrocortisone has a concentration in a range of about 0.5 mg/mL to about 1.5 mg/mL.

5. The composition of claim 4, wherein said regulated iron source comprises transferrin having a concentration in the range of about 2 mg/L to about 10 mg/L.

6. The composition of claim 5, wherein said concentration of transferrin is in a range selected from the group consisting of: about 2 mg/L to about 4 mg/L, about 3 mg/L to about 5 mg/L, about 4 mg/L to about 6 mg/L, about 5 mg/L to about 7 mg/L, about 6 mg/L to about 8 mg/L, about 7 mg/L to about 9 mg/L, and about 8 mg/L to about 10 mg/L.

7. The composition of claim 6, wherein said human serum albumin has concentration in a range of about 100 µg/mL to about 350 µg/mL.

8. The composition of claim 7, wherein said 5-hydroxytryptamine has a concentration in the range of about 0.001 g/L to about 0.003 g/L.

9. The composition of claim 8, wherein said electron transport activator comprises selenous acid having a concentration in the range of about 0.0000025 g/L to about 0.0000050 g/L.

10. The composition of claim 9, wherein said antioxidant comprises α-tocopherol acetate having a concentration in the range of about 0.0001 g/L to about 0.0003 g/L.

11. The composition of claim 10, wherein said antioxidant comprises ascorbic acid-2 phosphate having a concentration in the range of about 0.02 g/L to about 0.04 g/L.

12. The composition of claim 11, wherein said cell growth factor comprises human basic fibroblast growth factor having a concentration in the range of about 5 ng/mL to about 20 ng/mL.

13. The composition of claim 12, wherein said cell growth factor comprises platelet-derived growth factor bb having a concentration in the range of about 5 ng/mL to about 20 ng/mL.

14. The composition of claim 13, wherein said cell growth factor comprises epidermal growth factor having a concentration in the range of about 15 ng/mL to about 25 ng/mL.

15. The composition of claim 14, wherein said cell growth factor comprises insulin like growth factor-1 having a concentration in the range of about 2 ng/mL to about 10 ng/mL.

16. The composition of claim 15, wherein said cell growth factor comprises insulin having a concentration in a range about 0.004 g/L and about 0.006 g/L.

17. The composition of claim 16, wherein said phospholipid growth factor comprises lysophosphatidic acid having a concentration in the range of about 80 nM to about 200 nM.

18. The composition of claim 17, wherein said phospholipid growth factor comprises sphingosine 1-phosphate having a concentration in the range of about 80 nM and about 200 nM.

19. The composition of claim 18, wherein said one or more phospholipid growth factors has a concentration in a range selected from the group consisting of: about 100 nM to about 120 nM, about 110 nM to about 130 nM, about 120 nM to about 140 nM, about 130 nM to about 150 nM, about 140 nM to about 160 nM, about 150 nM to about 170 nM, about 160 nM to about 180 nM, and about 190 nM to about 200 nM.

20. The composition of claim 19, further comprising a transforming growth factor beta 1 having a concentration in a range of about 0.5 ng/mL to about 5 ng/mL.

21. The composition of claim 20, wherein said wingless/integrated 3a has a concentration in the range of about 20 ng/mL to about 200 ng/mL.

22. The composition of claim 21, wherein said R-spondin-1 has a concentration in the range of about 20 ng/mL to about 200 ng/mL.

23. A serum-free chemically defined cell culture medium composition, the composition comprising:
an amount of MCDB 201 medium of about 0.5 L/L;
an amount of Dulbecco's modified eagle medium of about 0.5 L/L;
an amount of sodium bicarbonate of about 3.7 g/L;
an amount of human serum albumin of about 0.25 g/L;
an amount of transferrin of about 0.005 g/L;
an amount of insulin of about 0.005 g/L;
an amount of selenous acid of about 0.0000037 g/L;
an amount of ascorbic acid-2phosphate of about 0.032205 g/L;
an amount of 5-hydroxytryptamine of about 0.002127 g/L;
an amount of dexamethasone of about 0.000003925 g/L;
an amount of hydrocortisone of about 0.001 g/L; and
an amount of α-tocopherol acetate of about 0.0002 g/L;
an amount of platelet-derived growth factor bb of about 10 ng/mL;
an amount of human basic fibroblast growth factor of about 10 ng/mL;
an amount of epiderman growth factor of about 20 ng/mL;
an amount of insulin like growth factor-1 of about 5 ng/mL;
an amount of lysophosphatidic acid of about 100 nM;
an amount of sphingosine 1-phosphate of about 150 nM;
an amount of human wingless/integrated 3a of about 20 ng/mL; and
an amount of R-spondin-1 of about 40 ng/mL.

\* \* \* \* \*